United States Patent [19]

Anderson et al.

[11] 4,403,035

[45] Sep. 6, 1983

[54] IN VITRO DNA-PROTEIN VIRAL ASSEMBLY AND GENE CLONING SYSTEM

[75] Inventors: Dwight L. Anderson; Bernard E. Reilly, both of Minneapolis, Minn.

[73] Assignee: Regents of the University of Minnesota, Minneapolis, Minn.

[21] Appl. No.: 275,242

[22] Filed: Jun. 19, 1981

[51] Int. Cl.³ .................... C12N 15/00; C12N 1/00; C12P 21/00

[52] U.S. Cl. .................. 435/172; 435/317; 435/68

[58] Field of Search .................... 735/172, 317, 235

[56] References Cited

U.S. PATENT DOCUMENTS 4,237,224  12/1980  Cohen et al. .................. 435/172

OTHER PUBLICATIONS

Kawamura et al., Molec. Gen. Genet. vol. 180, pp. 259–266, (1980).
Ito, J. of Vinology, vol. 28, pp. 895–904, (1978).
Anderson et al., Microbiology 1976, pp. 254–274.
Hagen et al., Journal of Virology, Aug. 1976, pp. 501–517.
Nelson et al., Journal of Virology, Aug. 1976, pp. 518–532.
Reilly et al., Journal of Virology, Oct. 1977, pp. 363–377.
Bjornsti et al., Proc. Natl. Acad. Sci. U.S.A., vol. 78, No. 9, pp. 5861–5865, Sep. 1981.
Bjornsti et al., Journal of Virology, Feb. 1982, pp. 508–517.

*Primary Examiner*—Alvin E. Tanenholtz
*Attorney, Agent, or Firm*—Burd, Bartz & Gutenkauf

[57] ABSTRACT

A method of packaging or encapsidating genetic material for use in gene transfer or cloning. An organism having a function or capability desired to be transferred or cloned is first selected. The DNA of this organism is extracted is cleaved to separate the exogenous genes controlling the function desired to be transferred or cloned. This exogenous gene is inserted in the linear DNA of a virus whose linear DNA has protein 5' termini, the virus DNA being extracted and cleaved so as to retain the genes specifying DNA replication. The resulting hybrid DNA is introduced into a cell-free in vitro medium along with a source of virus proheads and accessory viral structural and packaging proteins to assemble a hybrid virus encapsidating the hybrid DNA. This hybrid virus is similar in infectivity to the original or wild-type virus except that now either a segment of its DNA has been replaced by the desired exogeneous genes or the desired exogenous genes have been added to the viral DNA. The hybrid virus may then be used to infect microorganisms compatible with the virus to identify and select those changed microorganisms having the desired function or capability of the exogenous gene. These cells are then maintained and grown to produce in quantity those cloned microorganisms having the desired properties to produce useful products, hormones, enzymes, and the like.

13 Claims, 3 Drawing Figures

IN VITRO DNA-PROTEIN VIRAL ASSEMBLY AND GENE CLONING SYSTEM

The invention described herein was made in the course of work under a grant or award from the Department of Health and Human Services.

BACKGROUND OF THE INVENTION

1. Field of the Invention

This invention relates broadly to a new system for gene transfer and cloning. More particularly, this invention relates to a novel and more efficient method for the delivery of DNA (Deoxyribonuclei acid) genomic material for the introduction of a foreign function or capability into a host organism for expression, multiplication or replication. The method of this invention involves packaging or encapsidation of the hybrid DNA genomic material into a suitable viral vehicle or vector for transfer and delivery.

2. The Prior Art

The recently issued Cohen et al. U.S. Pat. No. 4,237,224 discloses a recombinant DNA cloning process. This process generally involves the steps of: (1) preparing a hybrid DNA (recombinant plasmid or plasmid chimera) incorporating a gene controlling a foreign function or capability, (2) transformation of a microorganism such as a bacterial cell with the hybrid DNA, (3) replicating the resulting transformed cell or transformant and isolating the hybrid DNA, and (4) utilizing the replicated hybrid DNA to transform the same or different microorganism by introducing the foreign function or capability and growing and multiplying these transformed cells. The hybrid DNA is prepared by inserting the desired foreign gene into a cleaved plasmid or virus DNA. Insertion of the hybrid DNA into a microorganism by transformation involves suspension in a medium of the hybrid DNA and microorganism cells under conditions conducive to the entry of DNA into the cells. However, effective entry of DNA into cells is rare, with the result that only a very small percentage of cells are transformed.

SUMMARY OF THE INVENTION

The present invention is directed to a novel and more efficient method of delivery and transfer of genetic information by packaging of a hybrid DNA-protein complex into a virus vehicle or vector, and the transfer of this genetic information by the hybrid virus into susceptible microorganisms. Broadly stated, the invention comprises a method of packaging or encapsidating replicating genetic material for use in gene transfer or cloning. The organism having a function or capability desired to be transferred is first selected. The DNA of this organism is extracted and cleaved to separate the exogenous genes controlling the function desired to be transferred or cloned. These exogenous genes are inserted in the DNA of a virus whose linear DNA has protein 5' termini, the viral DNA being extracted and cleaved so as to retain at least one of the 5'-ends and the genes controlling DNA replication. The resulting hybrid DNA-protein is introduced into a cell-free in vitro medium along with a source of viral capsid precursor structure, i.e. proheads, and required accessory viral structural and packaging proteins to assemble an infectious, hybrid virus encapsidating the hybrid DNA.

The viral capsid precursor structure, and accessory viral structural and packaging proteins, are produced by infecting compatible microorganisms with a first viral mutant capable of producing capsid precursor structures without producing at least one packaging protein and infecting compatible microorganisms with a second viral mutant capable of producing accessory viral structural and packaging proteins without producing capsid precursor structures. These infected cells are then mixed and lysed to provide the source of virus components for in vitro packaging of hybrid DNA-protein.

The hybrid virus is similar in infectivity to the original or wild-type virus except that either a segment of its DNA has been replaced by the desired exogenous genes or the desired exogenous genes have been added to the viral DNA. The hybrid virus is then used to infect microorganisms compatible with the virus to program the infected cells to serially reproduce the desired function or capability of the exogenous genes and the genes as nucleic acids. Although the process of the invention is applicable to viruses of plant or animal or microbial origin or specificity, whose linear DNA has protein 5' termini, it is described and illustrated with particular reference to a particular bacteriophage.

DETAILED DESCRIPTION OF THE PREFERRED EMBODIMENT

Figure 1:
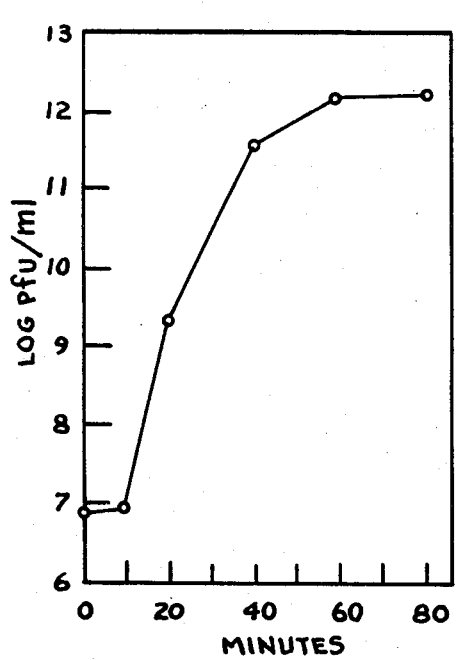
FIG. 1 is a graphic representation of the time course in phage production.

The process of this invention employs novel hybrid DNA molecules formed by the insertion of or the addition of foreign DNA having one or more genes into the genome of Bacillus bacteriophage $\phi 29$ or a related virus so that the 5'-termini of the hybrid molecule are bound to the covalently linked viral proteins known in $\phi 29$ as gene product 3, gp3. This protein, gp3, functions in both DNA replication and DNA packaging and viral assembly. This recombinant molecule will be referred to as hybrid DNA-gp3. This hybrid DNA-gp3 contains a gene or genes that express at least one phenotypic property of nonviral DNA and can be packaged or encapsidated into a hybrid virus. This hybrid virus can infect a bacterium compatible with the bacteriophage, the genes controlling viral replication function to ensure serial propagation of the hybrid DNA-gp3 and the cells produce the desired function or capability of the foreign or exogenous genes.

The process of this invention is divided into the following stages for description: (1) the preparation of the hybrid DNA-gp3; (2) in vitro packaging of the hybrid DNA-gp3; and (3) infection, and subsequent expression of the non-viral genes or recombinant DNA sequences in the recipient organism.

(1) Preparation of hybrid DNA-gp3

Bacterial viruses are programmed to ensure continued self replication in susceptible bacterial hosts. In some instances there is a minimal disruption of host macromolecule synthesis, and the virus can passively transfer genetic material from cell to cell. The desirable features of this viral DNA include the presence of proteins at the 5'-termini that promote effective in vitro DNA packaging and viral assembly, a capacity to insert or add exogenous genes, and the capacity to ensure replication of the hybrid DNA-gp3 in a fashion that permits host cell survival and propagation. The DNA-protein of φ29 can serve as a component of a vector or vehicle for genetic exchange or gene cloning because of a number of desirable features. (1) its DNA sequences can be cleaved to preserve the genes for DNA replication and a system (replicon) and provide ligatable termini for foreign DNA insertion; (2) this cleavage preserves the proteins and the base sequence at the 5'-termini that are essential for continuous DNA replication and DNA encapsidation; (3) it has a capacity to accept foreign, non-viral DNA that is sufficient to include an operon or set of genes with related or sequential function or that function as a unit.

Cleavage of the viral (vector) DNA and the "foreign" DNA to be inserted can be carried out together or separately by use of restriction endonucleases or other enzymes that generate ligatable cohesive termini or blunt ends. The methods and detailed conditions for cleavage, annealing, and ligation of DNA molecules can be found, e.g., in Methods in Enzymology, 68, 1979, Academic Press, Inc. (ed. Ray Wu). When necessary, specific fragments of viral or "foreign" DNA can be isolated, e.g., by centrifugation in an appropriate gradient or by electrophoresis in agarose. Viral DNA termini with covalently bound protein can be separated from internal DNA sequences by adsorption to glass fiber filters (Thomas et al, 1979, *Anal. Biochem.* 93, 158–166) and removal with sodium dodecyl sulfate (SDS).

In the subject process, host and viral DNA-gp3 are cleaved by a restriction endonuclease to generate ligatable termini. The hybrid DNA-gp3 can be generated by ligation, with or without the isolation of specific fragments of either foreign or viral DNA. Because cleavage sites are distributed throughout the viral genome or can be inserted into the viral genome, fragments of desired length can be generated by restriction endonuclease cleavage, and the fragments contain the desired base sequences and protein covalently bound to the 5'-termini. The DNA containing base sequences foreign to the viral DNA can be generated by cleavage by restriction nucleases and a population of hybrid DNA-gp3 molecules created by standard methods of ligation to restore the sugar phosphate backbone of the hybrid DNA-gp3. The selection of the restriction endonuclease and corresponding cleavage sites defines the size of the terminal fragments of the hybrid DNA-gp3, and the length restrictions imposed by the in vitro viral DNA packaging mechanism defines the mass of the foreign DNA sequence that can be added to or inserted between the terminal fragments.

(2) In vitro packaging of hybrid DNA-gp3

A hybrid DNA-gp3 of a compatible length and volume, corresponding roughly to the volume of a viral prohead and having the viral-specific protein, gp3, at the 5'-termini, can be efficiently packaged in vitro. This hybrid DNA-gp3 is added to a functioning in vitro assembly system that is packaging endogenous DNA-protein. In our experimental system, DNA-protein that is heat-released from virions can be repackaged when added to the complete complementation extract and is referred to as exogenous DNA. When hybrid DNA-gp3 is packaged for gene transfer, it is added to the complementation extract and is packaged and assembled into the hybrid virus in a fashion analogous to the repackaging of heat released viral DNA-gp3.

Our functional in vitro assembly or complementation system consists of two components. Component A is an extract of cells infected with a mutant that can produce viral proheads and DNA-protein. Component B is a source of the protein, gp16, that is essential for DNA-packaging, and DNA-protein. When these extracts are mixed, all proteins encoded in the viral genome are present in the extract in addition to proheads, the protein gp16 and DNA-protein.

During in vitro assemby up to 30% of the proheads accept DNA-gp3 during assembly, the DNA-gp3 from both parents are encapsidated with equal facility, and both genomes are proportionally represented in the progeny phage. The average yield during in vitro complementation exceeds 180 phage per prohead donor cell in the extract ($1 \times 10^{12}$ phage/ml), and in vitro assembly in very similar to in vivo maturation in terms of yield, intermediates and abortive structures. In virto complementation by a given mutant pair can exceed 50% of the yield of the corresponding in vivo complementation.

When DNA-gp3, released from the virion by heat, is added to a complementation extract as exogenous DNA, this DNA-gp3 is effectively repackaged along with the endogenous DNA-gp3. From 5–30% of the exogenous DNA-gp3 is repackaged in vitro and these viruses can constitute one-third of the total yield of viruses from the in vitro complementation. In our system there is no known distinction made between the repackaging of exogenous DNA in the packaging of endogenous DNA.

(3) Assembly, infection, replication and gene expression

The hybrid DNA-gp3 is added to an in vitro assembly extract and is packaged and assembled as though it were exogenous DNA extracted from the virion. This phase of the subject process can be used to package and assemble a hybrid DNA-gp3 containing foreign genes from any source of duplex DNA as long as they are bracketed by viral DNA-gp3.

The hybrid virus can infect any microorganism that φ29 can adsorb to or inject DNA into. The capsid of the hybrid virion can adsorb to the cell, and the hybrid DNA-gp3 can penetrate to the cytoplasm of the cell to be used to produce the gene or gene products selected or desired.

As the cell divides and reproduces, the viral genes ensure the replication of the hybrid DNA-gp3 at a rate to produce a copy number compatible with both survival of the hybrid DNA-gp3 in the cell population and production of enough foreign gene or gene product to detect by specific assay or to ensure production in commercial amounts.

The desired hybrid DNA-gp3 can be enriched for by selection of a cell population replicating the hybrid DNA-gp3 and packaging these hybrid DNA-gp3 molecules by in vitro assembly or by postinfection of the cells with wild-type helper phage or a suitable mutant. The new crop of hybrid phage can be isolated, separated and purified by standard methods and employed to introduce the desired hybrid DNA-gp3 molecule into the recipient cell in multiple copies in any number consistent with multiplicity of infection and the number of adsorption sites on the host microorganism.

The subject method can be used for any gene from any source which can be bracketed by viral DNA-protein and for which an assay of the gene or gene product exists. The foreign DNA can remain a part of a hybrid viral replicon or be integrated, when compatible, into the host genome. By selecting a replicon with a high copy number (this will vary depending upon the expression of resident viral genes), a wide variety of useful polypeptides, proteins and nucleic acids can be produced in quantity in nonpathogenic Bacilli, both sporogenous and asporogenous. Such useful products may include, for example, hormones, such as insulin, growth hormone, etc.; enzymes; serum proteins; and the like, as disclosed by Cohen et al., column 9, lines 12-53.

The invention is illustrated by the following examples:

EXAMPLE 1

In vitro assembly of bacteriophate φ29

Infectious φ29 was efficiently assembled in vitro in bacterial extracts containing viral proheads, DNA, and proteins serving structural and morphogenetic functions. The nonpermissive host Bacillus subtilis SpoA12 was grown to $6 \times 10^8$ cells/ml in Difco Antibiotic Medium #3 (PB). The cells were concentrated to $2 \times 10^9$/ml by centrifugation and infected with the phages sus16(300)-sus14(1241) or sus8(22)-sus10(302)-sus14(1241) in PB at an input multiplicity of 20. Both proheads and DNA accumulate during infection by the $16^-14^-$ mutant, and the recombinant $8^-10^-14^-$ was used as a source of gp16. In this latter infection, neither the major head protein, gp8, nor the upper collar protein, gp10, are made, and proheads cannot be assembled. After a 15 min adsorption period at 37° C. with shaking, the infected cells were treated with antisera (K value of 50) for 15 min, diluted to $2 \times 10^8$/ml with prewarmed PB, and incubated at 37° C. with shaking. Cells from the two mutant infections were combined at 85 min after infection, collected by centrifugation at ambient temperature and resuspended in 1/25 volume of the protoplasting medium SMMP(+BSA) (Chang et al., 1979, Molec. gen. Genet. 168, 111-115) supplemented with 100 mg/ml lysozyme and φ29 antisera (K value of 50). The SMMP(+BSA) medium consisted of equal volumes of 4× strength Difco Antibiotic Medium 3 (PB) and 2× strength SMM(+2% BSA) buffer, which contains 0.5 M sucrose, 0.02 M maleate, 0.02 M MgCl$_2$ (pH 6.5) and 2% (w/v) BSA. The concentrated cells were converted to protoplasts in 5 min at 40° C., washed by centifugation with unsupplemented SMMP(+BSA) medium, and lysed at 0° C. upon addition of reaction buffer at 1/50 the volume of the original culture. The reaction buffer consisted of 10 mM ATP (adjusted to pH 7.8 with ammonium hydroxide), 6 mM spermidine and 3 mM 2-mercaptoethanol in TMS buffer containing 0.05 M Trishydrochloride (pH 7.8), 0.1 M NaCl and 0.01 M MgCl$_2$. After about 5 to 10 min at 0° C., the reaction mixture was transferred to ambient temperature (0 time). Controls and complementation mixtures were incubated at ambient temperature for 80 to 120 min, and samples were plated in the standard bacteriophage assaay.

The results of in vitro assembly of φ29 are shown in Table 1.

TABLE 1

| Requirements for in vitro φ29 assembly | |
|---|---|
| Variation of the reaction mixture | Phage/ml × 10$^{-10}$ |
| Complete | 89[14] |
| Omit proheads | <0.001[4] |
| Omit gp16 | <0.001[3] |
| Add DNase at 5 μg/ml at 0 time | <0.001[8] |
| Add DNase at 5 μg/ml at 100 min | 95[4] |
| Add 20 mM EDTA | <0.01[1] |
| Add pyrophosphatase, 0.5 unit | <0.001[2] |

TABLE 1-continued

| Requirements for in vitro φ29 assembly | |
|---|---|
| Variation of the reaction mixture | Phage/ml × 10$^{-10}$ |
| Add 10 mM α-B-methyleneATP | <0.001[2] |
| Add 10 mM B-γ-methyleneATP | <0.001[2] |

The complete reaction mixture (200 ul) was an extract prepared by combining equal volumes of cells infected with the mutants $16^-14^-$ (supplying proheads and DNA) and $8^-10^-14^-$ (supplying gp16 and DNA) followed by lysis in TMS (50 mM Tris-HCl, pH 7.8—10 mM MgSO$_4$—100 mM Nacl) containing 10 mM ATP, 6 mM spermidine and 3 mM 2-mercaptoethanol. Incubation was at 23° C. for 80 to 120 min. Superscripts indicate the number of experiments used to compute the average values. In vivo complementation utilizing the same phages and conditions yielded approximately $2 \times 10^{12}$ pfu/ml at 0 time.

The average in vitro yield of $9 \times 10^{11}$ plaque-forming units/ml, compared to the in vivo complementation yield by these mutants of $2 \times 10^{12}$ pfu/ml, indicated that both processes have a similar efficiency. On the average the system generated 180 phage per cell equivalent of proheads, and on occasion 500 phage/cell were produced. Proheads, gp16 and DNA were essential for assembly.

The time course of in vitro phage production in this same in vitro complementation reaction mixture is shown in FIG. 1. Samples were removed at the indicated times and plated in the standard bacteriophage assay on the permissive host B. subtilis su$^{+44}$. Most DNA was packaged during the 10 to 40 min interval, and the maximum yield was obtained by 60 min (FIG. 1.).

Figure 2:
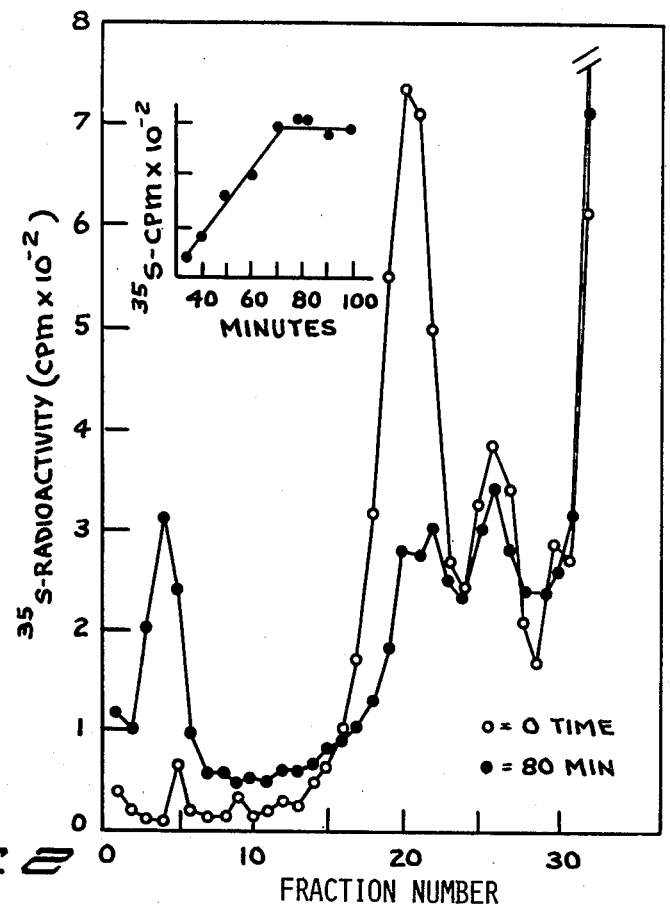
FIG. 2 is a graphic representation showing in vitro conversion of $^{35}S$-labeled proheads to phage.

Pulse-chase labeling experiments indicated that the prohead is converted to DNA-filled heads and φ29 (Nelson et al., 1976, J. Virol., 19, 518-532). We have examined in vitro complementation of the prohead to phage by sucrose gradient centrifugation. Cells infected with the sus mutants $16^-14^-$ or $8^-10^-14^-$ were labeled continuously with $^{35}$S-methionine (5 μCi/ml) from 30 to 70 min after infection, and labeling was terminated by the addition of excess unlabeled methionine and 50 μg/ml of chloramphenicol. The labeled cultures were mixed and lysed for in vitro complementation as described above, and the extract was split into two portions. Both were incubated at ambient temperature for 80 min; one was treated with 5 μg/ml of DNaseI at 0 time and the other with 5 μg/ml of DNaseI at 80 min. After centrifugtation at 12,000 g for 10 min at 4° C., 100 μl of each sample was layered on a linear gradient of 5% to 20% sucrose in TMS buffer and centrifuged at 35,000 rpm in the SW50.1 rotor at 23° C. for 30 min. TCA-insoluble radioactivity in each fraction of the gradient was determined. The results are shown in FIG. 2. Sedimentation is from right to left. Approximately 35% of the $^{35}$S-label in the prohead peak (centering on fraction 20) from the complementation extract at 0 time (o) shifted the position of phage (centering on fraction 4) after 80 min (o) of incubation. The particles in fraction 20 of the 0 time gradient had the morphology of proheads, and fractions 4 of the 80 min gradient contained φ29. The poorly resolved peaks at fractions 20 and 22 of the 80 min gradient contained mostly proheads and empty heads, respectively. These observations are consistent with results obtained during in vivo assembly (Nelson et al., supra).

We believe that we have demonstrated the in vitro packaging of DNA and the necessity for the prohead. The DNase sensitivity of the assembly and the kinetics and efficiency of the process suggest that the production of phage in surviving bacteria or in protoplasts infected with viral DNA is extremely unlikely (Table 1, FIG. 1, FIG. 2). Furthermore, extracts treated with restriction endonuclease HaeIII and centrifuged at 12,000×g for 10 min packaged more than $10^{11}$ phage/ml. The data of FIG. 2 demonstrate that DNase-resistant, infectious phage are produced in the presence of chloramphenicol from proheads radio-labeled prior to extract preparation.

Figure 3:
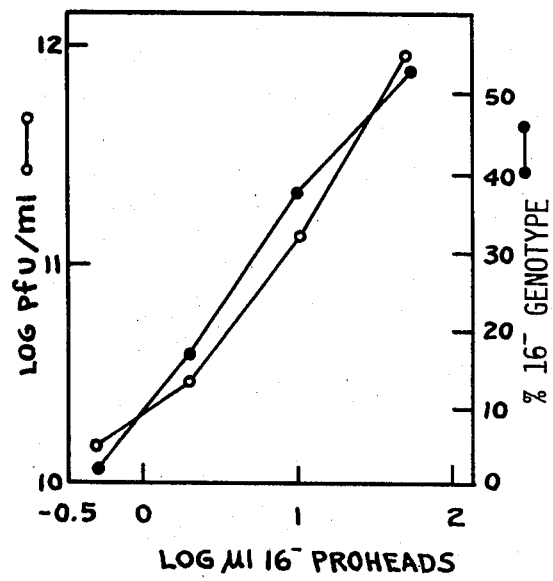
FIG. 3 is a graphic representation showing prohead dose response.

To evaluate prohead dose response, in vitro complementation extracts were prepared as described above from mixtures of various volumes of $16^-14^-$ infected cells and constant 50 μl volumes of $8^-10^-14^-$ infected cells, and the mixtures were incubated for 120 min at ambient temperature. The number of pfμ/ml was determined by plating in the standard bacteriophage assay, and the percentage of the $16^-14^-$ genotype packaged was nalyzed by qualitative complementation. The results are shown in FIG. 3. If the in vitro reaction involved dissociation and reassembly of proheads, one would expect phage production to show a strong dependence upon prohead concentration. It appears as if a constant proportion of added proheads are converted to phage over a hundred-fold dilution of proheads. In mixed extracts that assembled about 180 phage for each prohead donor cell (Table 1), both extracts contributed DNA equally (FIG. 3).

EXAMPLE 2

In vitro repackaging of exogenous φ29 DNA

Exogenous DNA molecules extracted from purified φ29 virions were efficiently repackaged in the in vitro system.

$^{35}$S-labeled wild-type or sus8.5(900)-sus14(1241) phage were grown in *B. subtilis* SpoA12 in M40 minimal medium (Tosi et al., 1975, *J. Virol.*, 16, 1282–1295) supplemented with 3 μg/ml L-methionine and containing 25 μCi/ml of $^{35}$S-methionine. After these phage were purified by banding in CsCl gradients, DNA was extracted by three methods: (1) phage were adsorbed to 6 mm Whatmann GF/C glass fiber filters and heated at 70° C. for 15 min in TES buffer (0.05 M Tris-HCl, pH 7.8–0.01 M EDTA—0.1 M NaCl) with additional NaCl added to give a final concentration of 0.4 M; DNA-protein was released from the filters with 1% SDS (Thomas et al., 1979, *Anal. Biochem.* 93, 158–166) and dialyzed against 0.01×TES; (2) phage were heated at 70° C. for 20 min in TE buffer (0.05 Tris-HCl, pH 7.8–0.01 M EDTA) and dialyzed against 0.01×TE; or (3) phage were heated for 7 min at 65° C. in TES buffer containing 1.2% (w/v) sarkosyl and 100 μg/ml phenylmethylsulfonylfluoride (PMSF), and the DNA-gp3 complex, containing about 1% of the total radioactivity of the virion, was isolated by centrifugation in a CsCl gradient containing 2.5 M guanidinium chloride; the complex was concentrated by adsorption to GF/C glass filters and released with 1% SDS as above; SDS-polyacrylamide gel electrophoresis (PAGE) and autoradiography of the Micrococcal nuclease-treated DNA-gp3 indicated that about 99% of the label was in gp3.

Exogenous φ29 DNA-protein was added to extracts prepared from mixtures of $8^-10^-14^-$- and $16^-14^-$-infected cells in the in vitro complementation assay. The results are shown in Table 2.

TABLE 2

| | In vitro repackaging of φ29 DNA* | | | |
|---|---|---|---|---|
| | Exogenous DNA | | | Exogenous + Endogenous |
| source+ | phage equivalents added/ml × $10^{-11}$ | DNA packaged (phage/ml × $10^{-11}$)++ | packaging efficiency (%) | Yield (phage/ml × $10^{-11}$)§ |
| DNA-gp3/capsids (glass fibers) | | | | |
| (1) heat/SDS/TES | 14 | 2.70 | 19.3 | 9.4 |
| DNA-gp3/capsids | | | | |
| (2) heat/TE | 13 | .29 | 2.2 | 1.7 |
| heat/TE | 8 | .41 | 5.1 | 3.8 |
| heat/TE | 17 | .72 | 4.2 | 4.0 |
| omit proheads | 17 | .006 | 0.04 | — |
| omit gp16 | 17 | .000001 | — | — |
| heat/TE | 17 | .43 | 2.5 | 3.0 |
| omit proheads | 17 | .009 | 0.05 | — |
| omit gp16 | 17 | .000001 | — | — |
| DNA-gp3 | | | | |
| (3) heat/sarkosyl/CsCl | 28 | .25 ‖ | 0.9 | 2.0 |

*The complete complementation mixture was used, except that proheads or gp16 were omitted in 2 experiments of the section DNA-gp3/capsids.
+Wild-type (1 and 2) or sus8.5(900)-sus14(1241) (3) DNAs were prepared from phage banded in CsCl gradients: (1) phage were adsorbed to 6 mm Whatman GF/C glass fiber filters and heated at 70° C. for 15 min in TES with 0.3M NaCl; DNA-protein was released from the filters with 1% SDS and dialyzed against 0.01X TES; (2) phage were heated at 70° C. for 20 min in TE and dialyzed against 0.01X TE; (3) $^{35}$S-phage were heated for 7 min at 65° C. in TES containing 1.2% (w/v) sarkosyl and 100 μg/ml PMSF, and the DNA-gp3 complex, containing about 1% of the total radioactivity of the virion, was isolated by centrifugation in a CsCl gradient containing 2.5M guanidinium chloride; the complex was concentrated by adsorption to GF/C glass filters and released with 1% SDS as above; SDS-PAGE and autoradiography of the Micrococcal nuclease-treated gp3-DNA indicated that about 99% of the label was in gp3.
++Determined by plating on the non-permissive host SpoA12 except for the virus sus8.5(900)-sus14(1241), determined as described below.
§Determined by plating on the permissive host su$^{+44}$.
‖ To estimate the number of assembled viruses with the genotype sus8.5(900)-sus14(1241), the complementation mixture was plated on the su$^{+3}$ permissive host (L15) to eliminate the $8^-10^-14^-$ phage (24%). Plaques were then transferred to the non-permissive host SpoA12, and 570/3530 clones (16.1%) were sus8.5(900)-sus14(1241); gp8.5 and gp14 are nonessential. Repackaged DNA is present in (2 × $10^{11}$ × 0.76 × 0.16) phage per ml.

About 19% of the wild-type DNA-protein added to the system was repackaged, and these wild-type genomes (2.7×$10^{11}$ pfμ/ml) were about 30% of the total DNA packaged. In a similar experiment, 29% of exogenous $^3$H-DNA molecules added to the complementation assay were assembled to give DNA-filled particles that were isolated on sucrose gradients.

However, the repackaging of DNA-protein released by heating phage in suspension was generally less efficient. About 4% of heat-released exogenous DNA-protein was repackaged, and these molecules accounted for more than 10% of those assembled during complementation (Table 2, DNA-gp3/capsids). There was an absolute requirement for gp16, but some DNA-protein was "repackaged" in the absence of proheads (8⁻10⁻14⁻ extract) (Table 2); qualitative complementation showed that more than 65% of this DNA was exogenous. When DNA-protein released by heat in the presence of 1% SDS was extracted by phenol and precipitated by 75% ethanol, about 1% of the phage equivalents of this DNA were repackaged.

To determine if capsid derived from the mature virion played a direct role in repackaging, $^{35}$S-gp3-DNA free of capsid proteins other than gp3, extracted by method (3) above, was added to the complete in vitro complementation mixture. About 0.9% of the molecules were repackaged, and these molecules were 12% of the total DNA packaged (Table 2). In these experiments, recombination is very rare; during complementation in 8⁻10⁻14⁻×16⁻14⁻ extracts, recombination was less than 0.002%.

The φ29 gene 3 product, covalently bound to the 5′-ends of the DNA, has been shown to have a vital role in effective packaging of DNA both in vivo and in vitro. Following is evidence for the in vitro role of gp3 in φ29 DNA encapsidation, based on trypsin sensitivity of the gp3-DNA.

Exogenous wild-type DNA-gp3 was extracted as described in method (2) above. The DNA-gp3 in 50 μl was treated with trypsin for 45 min at 37° C., and after incubation for 25 min at 37° C. with trypsin-inhibitor (7.5 μg), the mixture was added to 100 μl of the 16⁻14⁻×8⁻10⁻14⁻ in vitro complemetation extract described above in Example 1. As a control, trypsin (20 μg/ml) was pretreated with excess trypsin-inhibitor (7.5 μg) for 25 min at 37° C., added to the DNA-gp3, incubated for 45 min at 37° C., and added to the complementation extract. After 110 min at 23° C., the complementation mixture was plated on the su⁻ nonpermissive host to determine exogenous DNA-gp3 packaging and on the su⁺⁴⁴ permissive host to measure total assembly. The genotype of the sus progeny were determined by qualitative complementation. The results are shown in Table 3.

TABLE 3

The effect of trypsin treatment on DNA-gp3 in vitro assembly[a]

| Trypsin μg/ml | Assembly pfμ/ml × 10⁻¹⁰ | |
|---|---|---|
| | Experiment 1[b] | Experiment 2[c] |
| Control | 2.6 | 4.1 |
| 20 | 0.0001 | 0.0007 |
| 2 | 0.0012 | 0.26 |
| 0.2 | 2.1 | 1.0 |

[a]The exogenous wild-type DNA-gp3 in 50 μl was treated with trypsin for 45 min at 37° C., and after addition of an excess of trypsin-inhibitor (7.5 μg) and incubation for 25 min at 37° C., the mixture was added to 100 μl of the in vitro complementation extract prepared from equal amounts of cells infected with the mutants 16⁻14⁻ and 8⁻10⁻14⁻. For the control, trypsin (20 μg/ml) was pretreated with trypsin-inhibitor (7.5 μg) for 25 min at 37° C., after addition to the DNA-gp3, the mixture was incubated for 45 min at 37° C. After 110 min at ambient temperature, the complementation mixtures were plated on the su⁻ nonpermissive host to determine exogenous DNA-gp3 packaging and on the su⁺⁴⁴ permissive host to measure total assembly. The genotypes of the sus progeny were determined by qualitative complementation.
[b]In experiment #1, 1.3 ± 0.5 × 10¹¹ phage/ml were assembled, and 51% of 1357 sus phage were 16⁻14⁻. 25 μg/ml of exogenous wild-type φ29 DNA gave 2.6 × 10¹⁰ phage/ml (an efficiency of repackaging of 1.7%) and 20% of all phage assembled.
[c]In experiment #2, 3.8 ± 0.9 × 10¹¹ phage/ml were assembled and 46% of 2744 sus phage were 16⁻14⁻. 13.3 μg/ml of exogenous wild-type φ29 DNA gave 4.1 × 10¹⁰ phage/ml (an efficiency of repackaging of 5%) and 11% of all phage assembled.

EXAMPLE 3

In vitro packaging of biologically functional hybrid DNA-gp3 and introduction and function of the complex in a recipient cell Bacillus subtilis DNA containing gene sequences for uracil biosynthesis has been inserted between the protein-5′-termini of φ29 DNA, packaged as hybrid DNA-gp3 in vitro into DNase-insensitive φ29-like particles, and these particles used to infect and transform ura⁻ B. subtilis to prototrophy. Following are the detailed methods and results of this experiment.

For the preparation of B. subtilis SpoA12 DNA (ura⁺), cells were grown to 6×10⁸/ml in PB at 37° C., collected by centrifugation, resuspended in the same volume of 0.15 M NaCl—0.015 M sodium citrate (SSC), and lysed by addition of lysozyme to 50 μg/ml and incubation at 37° C. Pronase was added to 100 μg/ml, and following overnight incubation at 50° C., the mixture was filtered through a Millipore 0.45 μ dispo filter. The DNA was precipitated by addition of 3 volumes of ice-cold ethanol and resuspended in 0.01×TES buffer (1×TES is 0.05 M Tris-HCl, pH 7.8—0.1 M EDTA—0.1 M NaCl) at 1/10 the original volume. To prepare φ29 DNA, purified virions at 1.5×10¹²/ml in TE buffer (0.05 M Tris-HCl, pH 7.8—0.01 M EDTA) containing 1% SDS were heated for 2 min at 60° C., gently extracted with TE-saturated redistilled phenol, and the aqueous phase precipitated with 3 volumes of ice-cold ethanol. The precipitate was dissolved in 0.1×TE buffer and dialyzed against this buffer.

The B. subtilis and φ29 DNAs were cleaved with the restriction endonuclease EcoRl (purchased from Bethesda Research Laboratories) in a 50 μl reaction mixture containing 18 μg and 25 μg of DNA, respectively, 0.1 M Tris-HCl (pH 7.8), 0.05 M NaCl, 0.01 M MgCl₂, 0.001 M mercaptoethanol, and 1 unit of EcoRl endonuclease/μl at 37° C. for 1 hr. The cleaved DNAs were mixed to give 18 μg B. subtilis and 12.5 μg φ29 DNA in 75 μl, heated at 65° C. for 15 min to inactivate the endonuclease, and annealed in ice at 4° C. for 19 hrs. Dithiothreitol and ATP were added to final concentrations of 10 mM and 0.5 mM, respectively, and addition of 2.5 units of T4 DNA ligase was followed by incubation at 4° C. for 7 hrs and then at 15° C. for 48 hrs. The ligated mixture (50 μl) containing hybrid DNA-gp3 was added directly to the complete in vitro 16⁻14⁻×8⁻10⁻14⁻ complementation reaction mixture described in Example 1 above, and incubation was at 23° C. for 80 min. Hybrid phage derived from the in vitro complementation reaction were treated with DNaseI at 20 μg/ml for 15 min at 37° C. and used to infect the recipient B. subtilis BR13 (ura⁻try⁻) (2×10⁸ cells/ml) at estimated input multiplicities of 5 or 0.1. Following a 30 min adsorption and and incubation φ29 antiserum at 37° C., 100 μl samples of the infected cells were plated onto Spizizens minimal medium supplemented with 5 μg/ml of tryptophan and incubated at 37° C. for 24 to 72 hrs. On average one ura⁺ transductant was produced per 2×10⁵ infected cells.

The uracil-producing (ura⁺) clones were transferred on minimal medium supplemented with tryptophan in the presence of phage φ29 antiserum. Thus the hybrid DNA-gp3 was replicated and functional in the recipient cell and once introduced into the cell was independent of the viral capsid proteins and continued viral infection as evidenced by stability in the presence of viral antiserum which would neutralize the virus and prevent reinfection.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of encapsidating genetic material for use in gene transfer, which method comprises:
   (A) selecting $\phi 29$ a virus whose linear DNA has protein 5' termini,
   (B) selecting an organism having a metabolic or synthetic function desired to be transferred,
   (C) extracting and cleaving the $\phi 29$ DNA, retaining at least one protein 5' terminus and genes specifying DNA replication,
   (D) extracting and cleaving the DNA of the organism to be transferred, retaining the exogenous genes specifying the function desired to be transferred,
   (E) fusing said exogenous genes in the cleaved $\phi 29$ DNA to produce replicating hybrid linear $\phi 29$ DNA having at least one protein 5' terminus, and
   (F) providing in a cell-free in vitro medium a source of viral capsid precursor structures (proheads), accessory viral structural and packaging proteins and said hybrid $\phi 29$ DNA to assemble a hybrid virus encapsidating said hybrid DNA.

2. A method according to claim 1 wherein:
   (A) said hybrid virus encapsidating said hybrid $\phi 29$ DNA is introduced into a compatible microorganism to infect the same, and
   (B) the infected microorganisms are grown in order to identify and select those changed microorganisms having the metabolic or synthetic function desired to be transferred.

3. A method according to claim 2 wherein said changed microorganisms having the metabolic or synthetic function desired to be transferred are separated, maintained and grown to produce a quantity of cloned microorganisms having the desired metabolic or synthetic function.

4. A method according to claim 1 wherein:
   (A) a microorganism compatible with said virus is infected with said virus, and
   (B) said infected microorganism cells are lysed to provide said source of viral capsid precursor structure and accessory viral structural and packaging proteins.

5. A method according to claim 1 wherein:
   (A) a microorganism compatible with said virus is infected with a first viral mutant capable of producing viral capsid precursor structure (proheads) without producing packaging gene protein,
   (B) a microorganism compatible with said virus is infected with a second viral mutant capable of producing accessory viral structural and packaging proteins without producing capsid precursor structres, and
   (C) said infected cells are lysed to provide said source of capsid precursor structure and accessory viral structural and packaging proteins and all other viral induced proteins.

6. A method according to claim 1 wherein:
   (A) bacteria compatible with said $\phi 29$ is infected with said phage, and
   (B) said infected bacterial cells are lysed to provide said source of phage capsid precursor structure (proheads) and accessory phage structural and packaging proteins.

7. A method according to claim 1 wherein:
   (A) bacteria compatible with said $\phi 29$ is infected with a first suppressor-sensitive phage mutant capable of producing proheads without producing packaging gene protein,
   (B) bacteria compatible with said $\phi 29$ is infected with a second suppressor-sensitive phage mutant capable of producing accessory phage structural and packaging proteins without producing proheads, and
   (C) said infected cells are lysed to provide said source of phage proheads and accessory phage structural and packaging proteins and all other phage induced proteins.

8. A method according to claim 6 wherein said compatible bacteria is B. subtilis.

9. A method according to claim 7 wherein said compatible bacteria is B. subtilis said first mutant is sus $16^- 14^-$ and said second mutant is sus $8^- 10^- 14^-$.

10. A hybrid $\phi 29$ virus produced by the method of claim 1:
   (A) said hybride $\phi 29$ virus encapsidating hybrid DNA incorporating DNA extracted and cleaved from an organism having a metabolic or synthetic function desired to be replicated and including the exogenous genes specifying said function,
   (B) said incorporated DNA being fused into cleaved $\phi 29$ DNA having at least one protein 5' terminus and genes specifying replication, and
   (C) said hybrid $\phi 29$ virus being assembled in vitro from capsid viral precursor structural and packaging proteins and said hybrid DNA.

11. A method of encapsidating genetic material for use in gene transfer, which method comprises:
   (A) selecting a virus, bacteriophage $\phi 29$, whose linear DNA has protein 5' termini,
   (B) selecting an organism having a metabolic or synthetic function desired to be transferred,
   (C) extracting and cleaving the $\phi 29$ DNA, retaining at least one protein 5' terminus and genes specifying DNA replication,
   (D) extracting and cleaving the DNA of the organism to be transferred, retaining the exogenous genes specifying the function desired to be transferred,
   (E) fusing said exogenous genes in the cleaved $\phi 29$ DNA to produce replicating hybrid linear $\phi 29$ DNA having at least one protein 5' terminus,
   (F) infecting B. subtilis with a first suppressor sensitive $\phi 29$ mutant sus $16^- 14^-$ capable of producing proheads without producing packaging gene protein,
   (G) infecting B. subtilis with a second suppressor sensitive $\phi 29$ mutant sus $8^- 10^- 14^-$ capable of producing accessory $\phi 29$ structural and packaging proteins without producing proheads,
   (H) lysing said infected B. subtilis cells, and
   (I) in a cell-free in vitro medium, combining said lysed B. subtilis cells and said hybrid $\phi 29$ DNA to assemble a hybrid virus encapsulating said replicating hybrid $\phi 29$ DNA.

12. A method according to claim 11 wherein:

(A) said hybrid virus encapsidating said hybrid φ29 DNA is introduced into a compatible microorganism to infect the same,
(B) the infected microorganisms are grown in order to identify and select those changed microorganisms having the metabolic or synthetic function desired to be transferred, and
(C) said changed microorganisms having the metabolic or synthetic function desired to be transferred are separated, maintained and grown to produce a quantity of cloned microorganisms having the desired metabolic or synthetic function.

13. A hybrid φ29 virus produced by the method of claim 11:
(A) said hybrid φ29 virus encapsidating hybrid φ29 DNA incorporating DNA extracted and cleaved from an organism having a metabolic or synthetic function desired to be replicated and including the exogenous genes specifying said function,
(B) said incorporated DNA being fused into the cleaved DNA of φ29 having at least one protein 5' terminus and genes specifying replication, and
(C) said hybrid φ29 virus being assembled in vitro from capsid φ29 precursor structural and packaging proteins and said hybrid φ29 DNA.

* * * * *

UNITED STATES PATENT AND TRADEMARK OFFICE
CERTIFICATE OF CORRECTION

PATENT NO. : 4,403,035
DATED : September 6, 1983
INVENTOR(S) : Dwight L. Anderson et al It is certified that error appears in the above-identified patent and that said Letters Patent is hereby corrected as shown below:

On the title page, under OTHER PUBLICATIONS, line 3, "Vinology" should be --Virology--.

On the title page, under ABSTRACT, line 5, "is" should be --and--.

Column 4, line 15, "in" (first occurrence) should be --is--.

Column 4, line 16, "virto" should be --vitro--.

Column 9, line 10, after "capsid", --proteins-- is omitted.

Column 9, line 42, "complemetation" should be --complementation--.

Column 12, claims 10, line 3, "hybride" should be --hybrid--.

Signed and Sealed this

Twenty-ninth Day of November 1983

[SEAL]

Attest:

GERALD J. MOSSINGHOFF

Attesting Officer       Commissioner of Patents and Trademarks